United States Patent [19]

Takagi

[11] Patent Number: 4,665,959

[45] Date of Patent: May 19, 1987

[54] PLUG ASSEMBLY

[75] Inventor: Toshiaki Takagi, Fujinomiya, Japan

[73] Assignee: Terumo Kabushiki Kaisha, Tokyo, Japan

[21] Appl. No.: 786,242

[22] Filed: Oct. 9, 1985

[30] Foreign Application Priority Data

Oct. 15, 1984 [JP] Japan .................................. 59-215999

[51] Int. Cl.$^4$ ................................................ A61J 1/00
[52] U.S. Cl. ..................................... 141/330; 604/415;
604/905
[58] Field of Search ................. 141/329, 330; 604/415,
604/905

[56] References Cited

U.S. PATENT DOCUMENTS

| | | | |
|---|---|---|---|
| 3,495,594 | 2/1970 | Swanson | 141/330 X |
| 3,900,028 | 8/1975 | McPhee | 604/415 |
| 4,048,255 | 9/1977 | Hillier et al. | 604/415 X |
| 4,411,662 | 10/1983 | Pearson | 141/329 X |
| 4,479,989 | 10/1984 | Mahal | 604/415 X |
| 4,519,513 | 5/1985 | Weiler et al. | 604/415 X |

Primary Examiner—Stephen Marcus
Assistant Examiner—Mark Thronson
Attorney, Agent, or Firm—Frishauf, Holtz, Goodman & Woodward

[57] ABSTRACT

A plug assembly for puncture has a cylindrical member of a rigid resin having first and second openings one at each end thereof and a channel for communication between the first and second openings. The cylindrical member has a mating tapering surface on an outer side of the first opening. The assembly also includes an elastic member of a synthetic resin arranged at least in the channel extending toward the second opening of the cylindrical member so as to block the channel of the cylindrical member. The elastic member permits a needle penetration and assuring a re-sealability after an injection needle has been withdrawn. The cylindrical member and the elastic member are molded in an integral fashion.

14 Claims, 4 Drawing Figures

PLUG ASSEMBLY

BACKGROUND OF THE INVENTION

1. Field of the Invention:

This invention relates to a plug assembly and, in particular, to a puncture plug assembly adapted to permit an opening of a medical instrument, such as a retention needle and catheter, to be temporarily closed and to permit a fluid medicament to be injected through an injection needle into a human body, or to permit a body fluid, such as blood, to be taken from the human body, with the instrument being closed by the plug assembly.

2. Description of the Prior Art:

During the application of anesthesia, the transfusion of a liquid medicament and blood, the blood pressure measurement and the extracorporeal blood circulation, it is often required that a patient be moved from room to room of a hospital and from hospital to hospital and it is also required that an operation or treatment be temporarily interrupted. In this situation it will be necessary to retain or hold a needle or catheter in the blood vessel of the patient. At this time, use is made of a rubber plug assembly for puncture, in which a puncturable rubber is fitted over a rigid plug assembly, or a plug assembly for puncture in which a rubber plug is forced into a rigid plug body. It is often required that a liquid medicament such as a heparinized physiological sodium chloride solution be injected by, for example, an injection needle, as required, through the rubber with the plug assembly fitted into the base of a retention needle or a catheter.

FIG. 1 shows one example of a conventional plug assembly for puncture. This plug assembly comprises a plug body 1 and a rubber 2 for puncture. The plug assembly 1 has a double-walled cylinder section (3, 4) at a forward one-half section and a single-walled cylinder section at a rear one-half section 5. The puncture rubber 2 has a double-walled cylinder section (6, 7) coaxial with the plug body 1, and the cylinder section (6, 7) is covered over the plug body 1. The section 5 of the plug body 1 is fitted in a space between the walls 6 and 7 of the section (6, 7) so as to be held by a frictional resistance.

In the above-mentioned conventional plug assembly, however, a body fluid etc. are liable to be penetrated in a possible gap between the plug body 1 and the rubber 2 and, if this occurs, the frictional resistance therebetween is decreased due to the penetration of the body fluid. When, therefore, the injection needle penetrated into the rubber plug 2 is withdrawn from the plug assembly, the injection needle toegether with the rubber falls off, or if this is not the case a gap is created between the plug body 1 and the rubber 2, causing a fluid leakage.

SUMMARY OF THE INVENTION

It is accordingly the object of this invention to provide a plug assembly for puncture which is safe in function and assures a ready operability.

According to this invention there is provided a plug assembly for puncture, comprising a cylindrical member of a rigid resin having first and second openings one at each end thereof and a channel for communication between the first and second openings, the cylindrical member having a mating tapering surface on an outer side of the first opening, and an elastic member of a synthetic resin arranged at least in the channel extending toward the second opening of the cylindrical member so as to block the channel of the cylindrical member, the elastic member permitting a needle penetration and assuring a re-sealability after an injection needle has been withdrawn, in which the cylindrical member and elastic member are molded in an integral fashion.

Preferably, the cylindrical member is made of a rigid thermoplastic resin and the elastic member is made of a thermoplastic elastomer, both being heatfused or -sealed during the molding time. In this connection it is to be noted that the cylindrical member and elastic member are molded in an integral or one-piece fashion usually by using a two-color molding, an insert molding, a compression molding, or a cast molding method.

DETAILED DESCRIPTION OF THE PREFERRED EMBODIMENTS

Figure 1:
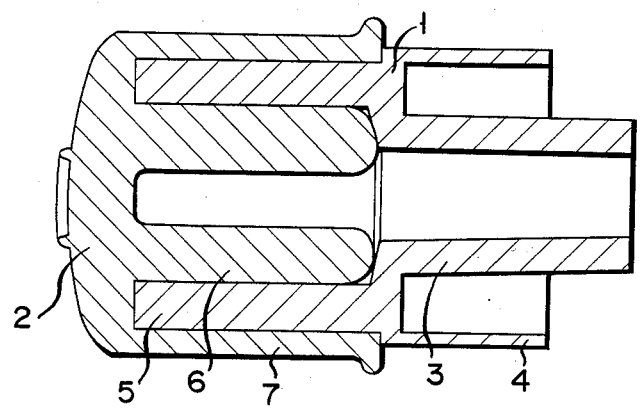
FIG. 1 is a cross-sectional view, as taken in an axial direction, showing a conventional plug assembly for puncture.

The embodiments of this invention will be explained below with reference to the accompanying drawing sheets. Identical reference numerals are employed to indicate identical or similar parts or elements throughout the specification.

Figure 2:
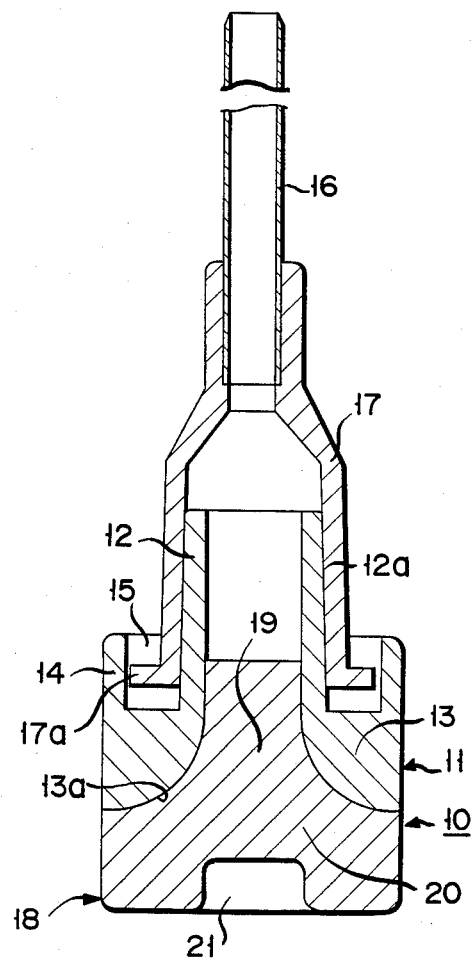
FIG. 2 is a cross-sectional view, as taken in an axial direction, showing a plug assembly for puncture according to a first embodiment of this invention.

A plug assembly 10 for puncture according to this invention comprises a cylindrical member 11 and elastic member 18. The cylindrical member 11 is made of a rigid thermoplastic resin, such as polypropylene, polycarbonate, polyvinyl chloride, polyethylene, acryl-stylene-base resin and acryl-butadiene-styrene. In particular, polypropylene is preferable for this usage. As indicated in FIG. 2, the cylindrical member 11 comprises a body 12 having the same inner diameter and including a lure-like mating surface 12a tapered toward an outer end and a mating portion 13 formed at the rear end of, and integral with, the body 12. In this connection it is to be noted that a hub of a retention needle 16, for example, is fitted over the mating surface 12a of the body 12 and that an elastic member 18 is inserted at the mating portion 13 into the cylindrical member. The mating portion 13 of the cylindrical member is so formed that the inner diameter is enlarged, while curved downward. An annular wall 14 is formed integral with the mating portion 13 of the member 11 such that it surrounds the lower portion of the body 12. An annular groove 15 is formed between the annular wall 14 and the body 12 of the member 11 to receive an annular flange 17a which is formed at the rear end of the retention hub.

The elastic member 18 is formed of a material, such as a thermoplastic elastomer, having an elasticity and re-sealability (that is, a possible gap formed by withdrawing a penetrated needle is re-sealed) and is heat-fused or sealed to the cylindrical member 11. The elastic member 18 and member 11 are molded in an integral or one-piece fashion. To explain a few examples, the elastic member 18 may be made of olefins, urethanes and styrene-based elastomers and, if the cylindrical member 12 is made of polypropylene, may be made preferably of olefin-based or styrene-based elastomer (e.g., styrene-butadiene-styrene copolymer) which is compatible with polypropylene.

The elastic member 18 comprises a forward end portion 19 having an outer surface complementary to the mating surface 13 of the member 11 and a cylindrical base portion 20 formed integral with the forward end portion 19. The neck portion of the forward end portion 19 is inserted partway into the cylindrical member 12. In the bottom surface of the base portion 20 a recess 21 is formed to provide a site for needle penetration. In this connection it is to be noted that the elastic member at the needle penetration site has such an adequate thickness as to assure a smooth needle penetration as well as a re-sealability.

The plug assembly 10 has, on an outer surface, only minimum possible stepped or projected portions, thus imparting only a least possible irritation to a human skin. For this reason, the annular wall 14, mating portion 13 and elastic member 18 are so formed as to have the same outer dimension.

As already set out, the cylindrical member 11 and elastic member 18 are formed integral with each other and are heat-fused or -sealed together at the molding time without the need of using a welding agent or a solvent. Therefore, there exists no gap between these members and thus there is no possibility that a fluid leakage will occur from the fused portion or that the elastic member 18 will fall off. Although a two-color molding, insert molding, compression molding, cast molding, etc. are known as a molding method, the two-color molding is preferable. Since, in this case, the holding member 11 is heat-fused or -sealed to the elastic member 18 at the molding time, it is preferred that a greater contact area is obtained therebetween. This is a reason why these members are curved to obtain a greater contact area.

Figure 3:
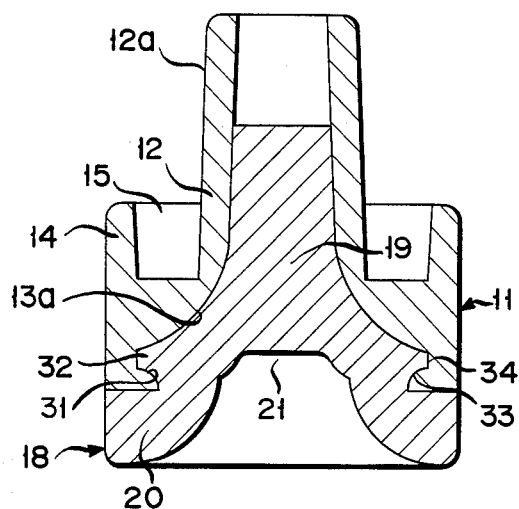
FIG. 3 is a cross-sectional view, as taken in an axial direction, showing a plug assembly for puncture according to a second embodiment of this invention.

A plug assembly of FIG. 3 is similar in arrangement to the plug assembly of FIG. 2, but different therefrom in that an engaging annular recess 31 is formed in that surface of the elastic member 18 which is in contact with a mating portion 13 of the cylindrical member 11 and an engaging annular projection 32 is so formed on the elastic member 18 so as to be located adjacent to the annular recess 31 and that the mating portion 13 has a corresponding, engaging annular projection 33 and corresponding, engaging annular recess 34. The annular recesses 31 and 34 and annular projections 32 and 33 provide a wedge effect. Even if, therefore, the elastic member 18 is merely in contact with the cylindrical member 11 without being heat-fused during an integral molding time, these annular recesses and projections assure an intimate contact and positive seal therebetween. This advantage is also obtained even when both the members are heat-fused together.

Figure 4:
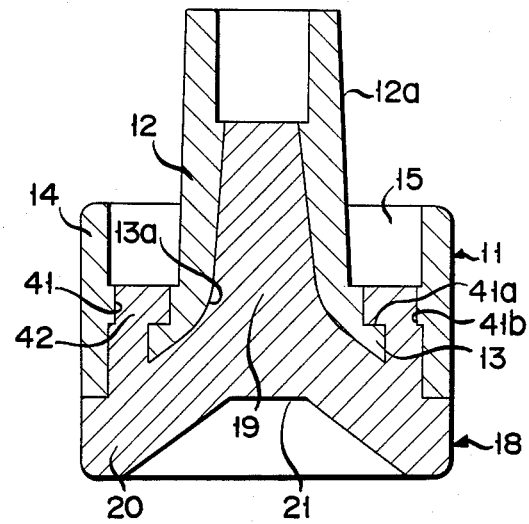
FIG. 4 is a cross-sectional view, as taken in an axial direction, showing a plug assembly for puncture according to a third embodiment of this invention.

A plug assembly of FIG. 4 is similar to that of FIG. 2, except that a plurality of engaging holes 41 are formed at an insertion end portion of the elastic member 18. The engaging holes 41 are opened at the bottom of an annular recess 15 and have steps 41a and 41b and that projections 42 are formed an elastic member 18 so as to correspond to the engaging holes 41. The engaging holes 41 and engaging projections 42 provide the same advantages as the annular recesses 31, 34 and annular projections 32, 33 as shown in FIG. 3.

The so-constructed plug assembly for mixed-fluid injection may be used as a temporary plug assembly for an intravenous retention needle or as mixed-fluid injection inlet for liquid medicament. The plug assembly may also be used reliably as a three-way stopcock, as a plug assembly for catheters such as a liquid transfusion device or a gastric tube and as a mixed-fluid injection type plug assembly for injecting a heparinized physiological sodium chloride solution, liquid transfusion agent and so on, without involving a fall of a puncturing section or a liquid leakage.

When a thermoplastic elastomer is used as a material for mixed-fluid injection outlet, it is possible to reduce a penetration resistance at the puncture time, to provide a better re-sealability and to provide a better integral moldability.

A plug assembly for puncture, according to this invention, has the following advantages:

(1) It is possible to provide an integral molding in a two-color mode in spite of using a different material for a cylindrical body having a lure-like taper and for an elastic member having a needle penetration section.

(2) It is possible to provide an easy-to-handle plug assembly which requires no post-working.

(3) There is no possibility that there will be a liquid leakage or that a rubber cap will fall off.

(4) It is possible to reduce penetration resistance and to lower manufacturing cost.

What is claimed is:

1. A plug assembly for puncture, comprising:
a cylindrical member of a rigid resin having first and second openings one at each end thereof, and a channel for communication between the first and second openings, said cylindrical member having a mating outwardly tapering surface on an outer side of the first opening; and
an elastic solid member of a synthetic resin having a neck portion, a flared portion integral with said neck portion, and a recess formed in the bottom of said flared portion, said recess providing a needle penetration site, said neck portion and said flared portion defining an outer surface corresponding in shape to and matingly engaging with said mating outwardly tapering surface of said cylindrical member, said neck portion being arranged at least in the portion of the channel adjacent the first opening of the cylindrical member and extending toward the section opening so as to block the channel of the cylindrical member, said elastic member permitting an injection needle penetration beginning at the recess thereof and extending therethrough, and being sufficiently elastic to assure a re-sealability after the injection needle has been withdrawn therefrom;
said cylindrical member and said elastic member being molded together in an integral fashion to form a single unit, said cylindrical member and said elastic member being heat-fused at their mutual contact surfaces during said molding together to provide a liquid-tight seal at said contact surfaces.

2. A plug assembly according to claim 1, in which said cylindrical member is made of a rigid thermoplastic resin and said elastic member is made of a thermoplastic elastomer.

3. A plug assembly according to claim 1, in which engaging means is provided on respective contact surfaces of said cylindrical member and said elastic member to improve engagement therebetween.

4. A plug assembly according to claim 3, in which said engaging means comprises a recess and a projection formed on said cylindrical member, and a corresponding projection and recess formed on said elastic member so as to engage with said recess and projection, respectively, of said cylindrical member.

5. A plug assembly according to claim 3, in which said engaging means comprises a through hole formed in the second opening of said cylindrical member, and a projection formed on said elastic member so as to correspond to and be engagable with said through hole.

6. A plug assembly according to claim 1, in which said cylindrical member has a curved surface where it is in contact with a corresponding surface of said elastic member.

7. A plug assembly according to claim 1, in which said cylindrical member has an outwardly curved mating tapering surface curving outwardly from said channel toward an outer peripheral portion thereof, and wherein said flared portion defines an outer surface corresponding in shape to said outwardly curved mating tapering surface of said cylindrical member.

8. A plug assembly for puncture, comprising:
a cylindrical member of a rigid resin having first and second openings one at each end thereof, and a channel for communication between the first and second openings, said cylindrical member having a mating outwardly tapering surface on an outer side of the first opening; and
an elastic solid member of a synthetic resin having a neck portion, a flared portion integral with said neck portion, and a recess formed in the bottom of said flared portion, said recess providing a needle penetration site, said neck portion and said flared portion defining an outer surface corresponding in shape to and matingly engaging with said mating outwardly tapering surface of said cylindrical member, said neck portion being arranged at least in the portion of the channel adjacent the first opening of the cylindrical member and extending toward the second opening so as to block the channel of the cylindrical member, said elastic member permitting an injection needle penetration beginning at the recess thereof and extending therethrough, and being sufficiently elastic to assure a re-sealability after the injection needle has been withdrawn therefrom;
said cylindrical member and said elastic member being molded together in an integral fashion to form a single unit, said cylindrical member and said elastic member being heat-sealed at their mutual contact surface during said molding together to provide a liquid-tight seal at said contact surfaces.

9. A plug assembly according to claim 8, in which said cylindrical member is made of a rigid thermoplastic resin and said elastic member is made of a theremoplastic elastomer.

10. A plug assembly according to claim 8, in which engaging means is provided on respective contact surfaces of said cylindrical member and said elastic member to improve engagement therebetween.

11. A plug assembly according to claim 10, in which said engaging means comprises a recess and a projection formed on said cylindrical member, and a corresponding projection and recess formed on said elastic member so as to engage with said recess and projection, respectively, of said cylindrical member.

12. A plug assembly according to claim 10, in which said engaging means comprises a through hole formed in the second opening of said cylndrical member, and a projection formed on said elastic member so as to correspond to and be engable with said through hole.

13. A plug assembly according to claim 10, in which said cylindrical member has a curved surface where it is in contact with a corresponding surface of said elastic member.

14. A plug assembly according to claim 8, in which said cylindrical member has an outwardly curved mating tapering surface curving outwardly from said channel toward an outer peripheral portion thereof, and wherein said flared portion defines an outer surface corresponding in shape to said outwardly curved mating tapering surface of said cylindrical member.

* * * * *

UNITED STATES PATENT AND TRADEMARK OFFICE
CERTIFICATE OF CORRECTION

PATENT NO. : 4,665,959

DATED : May 19, 1987

INVENTOR(S) : T, TAKAGI

It is certified that error appears in the above-identified patent and that said Letters Patent is hereby corrected as shown below:

Column 2, line 42, "base" should read -- based --

Column 6, line 10, "surface" should read -- surfaces --

Column 6, line 31, "according to claim 10" should read

-- according to claim 8 --

Signed and Sealed this

Ninth Day of August, 1988

Attest:

DONALD J. QUIGG

Attesting Officer

Commissioner of Patents and Trademarks